(12) United States Patent
Chinchoy et al.

(10) Patent No.: US 12,310,733 B2
(45) Date of Patent: *May 27, 2025

(54) INTRAUTERINE ACCESS CATHETER FOR DELIVERING AND FACILITATING OPERATION OF A MEDICAL APPARATUS FOR ASSISTING PARTURITION

(71) Applicant: 3VO Medical, Inc., Los Angeles, CA (US)

(72) Inventors: Ed Chinchoy, Rancho Palos Verdes, CA (US); James Kelley, Coon Rapids, MN (US); Jay Snell, Los Angeles, CA (US)

(73) Assignee: 3VO Medical, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/544,185

(22) Filed: Dec. 18, 2023

(65) Prior Publication Data
US 2024/0156384 A1 May 16, 2024

Related U.S. Application Data

(63) Continuation of application No. 17/180,668, filed on Feb. 19, 2021, now Pat. No. 11,877,850, which is a
(Continued)

(51) Int. Cl.
*A61B 5/24* (2021.01)
*A61B 5/00* (2006.01)
(Continued)

(52) U.S. Cl.
CPC ............... *A61B 5/24* (2021.01); *A61B 5/035* (2013.01); *A61B 5/065* (2013.01); *A61B 5/4356* (2013.01);
(Continued)

(58) Field of Classification Search
None
See application file for complete search history.

(56) References Cited

U.S. PATENT DOCUMENTS 3,230,953 A  1/1966  Birnberg et al.
3,918,444 A  11/1975  Hoff
(Continued)

OTHER PUBLICATIONS

PCT/US2016/061354. International Preliminary Report on Patentability (Jan. 18, 2018).
(Continued)

*Primary Examiner* — Rene T Towa
*Assistant Examiner* — Matthew Eric Ogles
(74) *Attorney, Agent, or Firm* — LOZA & LOZA, LLP; David S. Sarisky (57) ABSTRACT

A system for augmenting uterine forces includes a medical apparatus having a balloon body that transitions between a compacted state and an expanded state, a catheter that receives the medical apparatus and obtains electrical signals indicative of intrinsic uterine contractions, and a controller coupled to the catheter to receive the electrical signals, and to a source of an agent. The controller processes the electrical signals to detect an onset of an intrinsic uterine contraction, an increase in uterine contraction forces, or a decrease in uterine contraction forces. In response to a detection of an onset of an intrinsic uterine contraction or an increase in uterine contraction forces, the controller causes an agent to be delivered from the agent source to the balloon body to expand the balloon body. In response to a detection of a decrease in uterine contraction forces, the controller causes agent to discharge from the balloon body to collapse the balloon body.

7 Claims, 8 Drawing Sheets

Related U.S. Application Data continuation of application No. 16/127,181, filed on Sep. 10, 2018, now Pat. No. 10,925,501, which is a continuation of application No. 14/942,577, filed on Nov. 16, 2015, now Pat. No. 10,105,070.

(60) Provisional application No. 62/080,511, filed on Nov. 17, 2014, provisional application No. 62/080,506, filed on Nov. 17, 2014.

(51) Int. Cl.
*A61B 5/03* (2006.01)
*A61B 5/06* (2006.01)
*A61B 17/00* (2006.01)
*A61B 17/42* (2006.01)

(52) U.S. Cl.
CPC .......... *A61B 5/4836* (2013.01); *A61B 5/6852* (2013.01); *A61B 5/6853* (2013.01); *A61B 17/4241* (2013.01); *A61B 2017/00292* (2013.01); *A61B 2017/00557* (2013.01)

(56) References Cited

U.S. PATENT DOCUMENTS

| | | |
|---|---|---|
| 3,948,270 A | 4/1976 | Hasson |
| 4,089,337 A | 5/1978 | Kronner |
| 4,136,681 A | 1/1979 | Hon |
| 4,252,131 A | 2/1981 | Hon |
| 4,338,943 A | 7/1982 | Okamoto |
| 4,349,033 A | 9/1982 | Eden |
| 4,490,421 A | 12/1984 | Levy |
| 4,533,345 A | 8/1985 | Louw |
| 4,722,730 A | 2/1988 | Levy |
| 4,775,362 A | 10/1988 | Kronner |
| 4,873,986 A | 10/1989 | Wallace |
| 4,890,623 A | 1/1990 | Cook et al. |
| 4,901,735 A | 2/1990 | Von Berg |
| 4,906,244 A | 3/1990 | Pinchuk et al. |
| 4,944,307 A | 7/1990 | Hon et al. |
| 4,976,692 A | 12/1990 | Atad |
| 4,996,974 A | 3/1991 | Ciarlei |
| 5,156,590 A | 10/1992 | Vilmar |
| 5,156,612 A | 10/1992 | Pinchuk et al. |
| 5,247,932 A | 9/1993 | Chung et al. |
| 5,279,308 A | 1/1994 | Disabito et al. |
| 5,304,131 A | 4/1994 | Paskar |
| 5,304,197 A | 4/1994 | Pinchuk et al. |
| 5,318,526 A | 6/1994 | Cohen |
| 5,373,852 A | 12/1994 | Harrison et al. |
| 5,377,673 A | 1/1995 | Van Dell et al. |
| 5,405,356 A * | 4/1995 | Hahn ............ A61B 17/42 600/588 |
| 5,449,371 A | 9/1995 | Pinchuk et al. |
| 5,507,725 A | 4/1996 | Savage et al. |
| 5,522,400 A | 6/1996 | Williams |
| 5,566,680 A | 10/1996 | Urion et al. |
| 5,573,007 A | 11/1996 | Bobo, Sr. |
| 5,624,399 A | 4/1997 | Ackerman |
| 5,738,653 A | 4/1998 | Pinchuk et al. |
| 5,741,320 A | 4/1998 | Thornton et al. |
| 5,785,053 A | 7/1998 | Mcandrew et al. |
| 5,865,800 A | 2/1999 | Mirarchi et al. |
| 5,865,801 A | 2/1999 | Houser et al. |
| 5,947,991 A | 9/1999 | Cowan |
| 5,951,497 A * | 9/1999 | Wallace ............ A61B 5/035 600/176 |
| 5,984,879 A | 11/1999 | Wallace et al. |
| 5,991,649 A | 11/1999 | Garfield et al. |
| 6,002,968 A | 12/1999 | Edwards |
| 6,036,697 A | 3/2000 | Dicaprio |
| 6,110,142 A | 8/2000 | Pinchuk et al. |
| 6,129,737 A | 10/2000 | Hamilton et al. |
| 6,146,355 A | 11/2000 | Biggs |
| 6,231,524 B1 | 5/2001 | Wallace |
| 6,356,777 B1 | 3/2002 | Garfield et al. |
| 6,395,012 B1 | 5/2002 | Yoon et al. |
| 6,434,418 B1 | 8/2002 | Neal et al. |
| 6,520,977 B2 | 2/2003 | Piraka |
| 6,522,933 B2 | 2/2003 | Nguyen |
| 6,592,550 B1 | 7/2003 | Boatman et al. |
| 6,648,842 B2 | 11/2003 | Horkel |
| 6,676,680 B1 | 1/2004 | Packer |
| 6,694,192 B2 | 2/2004 | Policker et al. |
| 6,743,227 B2 | 6/2004 | Seraj et al. |
| 6,802,825 B2 | 10/2004 | Ackerman et al. |
| 6,827,703 B1 | 12/2004 | Ackerman |
| 6,843,251 B1 | 1/2005 | Huerland et al. |
| 6,879,858 B1 | 4/2005 | Adams |
| 6,979,312 B2 | 12/2005 | Shimada |
| 7,029,467 B2 | 4/2006 | Currier et al. |
| 7,144,379 B2 * | 12/2006 | Belli .................. A61B 5/4356 600/587 |
| 7,220,252 B2 * | 5/2007 | Shah ................ A61M 25/1027 604/101.02 |
| 7,309,324 B2 | 12/2007 | Hayes et al. |
| 7,333,844 B2 | 2/2008 | Jones et al. |
| 7,481,774 B2 | 1/2009 | Brockway et al. |
| 7,695,451 B2 | 4/2010 | Bencini et al. |
| 7,708,716 B2 | 5/2010 | Shah et al. |
| 7,720,517 B2 | 5/2010 | Drysen |
| 8,123,773 B1 | 2/2012 | Shirley |
| 8,206,343 B2 | 6/2012 | Racz |
| 8,221,401 B2 | 7/2012 | Sharkey et al. |
| 8,292,901 B2 | 10/2012 | Auerbach et al. |
| 8,491,503 B2 | 7/2013 | Zaiken et al. |
| 8,597,306 B1 | 12/2013 | Blurton et al. |
| 8,606,371 B2 | 12/2013 | Garfield et al. |
| 8,690,873 B2 | 4/2014 | Truckai et al. |
| 8,900,215 B2 | 12/2014 | Pepper et al. |
| 8,939,990 B2 | 1/2015 | Nguyen |
| 8,945,025 B2 | 2/2015 | Olson et al. |
| 8,972,028 B2 | 3/2015 | Garfield et al. |
| 9,504,440 B2 | 11/2016 | Hart |
| 9,724,036 B2 | 8/2017 | Broens |
| 10,105,070 B2 | 10/2018 | Chinchoy |
| 10,925,501 B2 | 2/2021 | Chinchoy et al. |
| 2005/0038421 A1 | 2/2005 | Joye et al. |
| 2008/0300571 A1 | 12/2008 | Lepivert |
| 2011/0082488 A1 | 4/2011 | Niazi |
| 2012/0109177 A1 | 5/2012 | Ulmer |
| 2013/0190796 A1 | 7/2013 | Tilson et al. |
| 2013/0253466 A1 | 9/2013 | Campbell et al. |
| 2013/0261702 A1 | 10/2013 | Garfield et al. |
| 2014/0277053 A1 | 9/2014 | Wang et al. |

OTHER PUBLICATIONS

PCT/US2016/061429. International Preliminary Report on Patentability (Jan. 18, 2018).
PCT/US2016/061429. International Search Report & Written Opinion (Mar. 24, 2017).
European Patent Appln. No. 16866883.8. Extended European Search Report (Apr. 8, 2019).

* cited by examiner

INTRAUTERINE ACCESS CATHETER FOR DELIVERING AND FACILITATING OPERATION OF A MEDICAL APPARATUS FOR ASSISTING PARTURITION

CROSS-REFERENCE TO RELATED APPLICATIONS

This application is a continuation application of U.S. patent application Ser. No. 17/180,668, filed Feb. 19, 2021, for "Intrauterine Access Catheter for Delivering and Facilitating Operation of a Medical Apparatus for Assisting Parturition," now U.S. Pat. No. 11,877,850, which is a continuation application of U.S. patent application Ser. No. 16/127,181, filed Sep. 10, 2018, for "Intrauterine Access Catheter for Delivering and Facilitating Operation of a Medical Apparatus for Assisting Parturition," now U.S. Pat. No. 10,925,501, which is a continuation application of U.S. patent application Ser. No. 14/942,577, filed Nov. 16, 2015, for "Intrauterine Access Catheter for Delivering and Facilitating Operation of a Medical Apparatus for Assisting Parturition," now U.S. Pat. No. 10,105,070, which claims the benefit of U.S. Provisional Application Ser. No. 62/080,506, entitled "Birthing Assistance Catheter" filed on Nov. 17, 2014, and U.S. Provisional Application Ser. No. 62/080,511, entitled "Intracorporeal Birthing Device" filed on Nov. 17, 2014, each of which is expressly incorporated by reference herein in its entirety.

This application includes subject matter related to U.S. patent application Ser. No. 14/942,748, entitled "Intrauterine Balloon Apparatus, System, and Method for Augmenting Uterine Birthing Forces During Parturition", filed on Nov. 16, 2015, now U.S. Pat. No. 10,260,595, which is expressly incorporated by reference herein in its entirety.

TECHNICAL FIELD

The present disclosure relates to a catheter and more particularly, an intrauterine catheter for accessing and navigating the uterine cavity, infant, placenta and umbilical cord to deliver a medical apparatus at a proximal uterine location for assisting infant descent during active labor or parturition.

BACKGROUND

There are three physiologic stages of labor during the intrapartum process of natural childbirth. The first stage is latent labor and begins when the uterine muscles begin to tighten (contract) and relax in a periodic manner. These early contractions occur at an irregular frequency each lasting for less than a minute and are known to be uncomfortable for the mother. The total duration of this first phase is highly variable and last from several hours to several days. Over time frequency of the contractions becomes more regular and grows with intensity, resulting in increased intrauterine pressures and associated pain, causing greater downward forces towards the infant and birth canal leading to the thinning (effacing) and opening (dilation) of the cervix.

The second stage is active labor and begins when the mother's uterine contractions become more regular and frequent, generating sufficient coordinated strength towards the infant and birth canal causing the cervix to become thinner and diameter to grow larger for the infant to begin descending down the birth canal. The combination of intensifying uterine contractions, increased intrauterine pressures, and reduced birth canal resistance promotes gradual infant descent through the birth canal until it is eventually delivered or surgically extracted. The duration of this stage lasts several hours and is associated with active infant movement and significant maternal pain. The third stage follows the delivery of the infant after which uterine contractions and the intrapartum process continues resulting in the expulsion of the placenta.

Difficulties often arise during the first and second stage when the mother's uterus is unable to generate the required contractility to initiate and ensure steady progression of the infant down the birth canal. Furthermore, increased resistance to infant descent by the mother's pelvic region along the birth or cervical canal requires greater effective birthing forces to ensure infant descent. A significant percentage of women therefore experience prolonged durations of labor which subsequently extends morbidity and increases the risks to both her and her infant due to extended physical stress.

A significant clinical need exists to manage intrauterine birthing forces for the purposes of assisting, stabilizing, or accelerating the birthing process during the first and second stage of labor. Currently, when a mother experiences prolonged durations of labor, the mainstay pharmacologic intervention used is synthetic Oxytocin (Pitocin) for stimulating and increasing uterine contractions. Dosages are based on protocols derived from a combination of population data and individual patient assessments of contraction rates and birthing progress, but individual patient's intrauterine pressures are generally not optimized on a per case basis. Although a very small minority of patients do receive intrauterine pressure monitors for titrating titrating Oxytocin, labor management using individual pressure optimization is not widely accepted due in large part to data suggesting pharmacologic interventions are limited with their effectiveness to achieve sufficient pressures. Other methods of assisting the birthing process include prostaglandins and Pessary cervical dilators to reduce the resistance of the birth canal to infant descent but do not compensate for ineffective uterine contractions.

In totality these interventions prove to be only marginally effective, and a significant percentage of mothers attempting natural births eventually undergo a surgical extraction of the infant (Cesarean) through a transverse abdominal incision to directly access the uterine cavity. Because Cesarean surgical interventions are highly invasive and result in extensive maternal morbidity, an increase of recovery times, and significantly greater risks of uterine injury with future subsequent births, a clinical need exists for providing an alternative option in lieu of a Cesarean section intervention by safely enhancing uterine descent forces and reducing labor durations.

SUMMARY

Disclosed herein is a minimally invasive catheter and method for gaining access to a proximal region of the uterus for the purposes of delivering, deploying and operating an intrauterine medical apparatus to assist infant descent during natural child birth. The catheter is configured to gain access to the intrauterine cavity through the cervical canal, to navigate the intrauterine cavity containing the infant, placenta and umbilical cord, and to place the medical apparatus between the endometrium and infant at a proximal uterine location near the fundus. The catheter provides a conduit for the medical apparatus and serves as a platform for one or more sensors to monitor physiologic intrauterine and fetal indicators of parturition progress.

In one aspect, a catheter for directing an intrauterine medical apparatus within a patient's cervix includes a handle having a proximal end, a distal end, and a port at the proximal end. The catheter also includes an elongated body having a proximal section, a distal section, and a port at a distal tip of the distal section. An inner lumen extends from the distal tip of the elongated body to the port at the proximal end of the handle. The inner lumen is configured to slidably receive the intrauterine medical apparatus through the port at the proximal end of the handle. The elongated body is constructed such that the distal section includes a distal portion and a proximal portion, wherein the distal portion is more flexible than the proximal portion, and the proximal portion is more flexible than the proximal section of the elongated body. The elongated body is further constructed such that at least one of the distal portion and proximal portion is configured to bend to facilitate entry within the patient's cervix.

In another aspect, an intrauterine system includes a medical apparatus configured for placement in an intrauterine cavity at a location between an infant and uterine walls. The system also includes a catheter configured to place, e.g., navigate and deliver, the medical apparatus through a patient's cervix. The catheter includes a handle having a proximal end, a distal end, and a port at the proximal end; and an elongated body having a proximal section, a distal section, and a port at a distal tip of the distal section. An inner lumen extends from the distal tip of the elongated body to the port at the proximal end of the handle. The inner lumen is configured to slidably receive the medical apparatus through the port at the proximal end of the handle.

In yet another aspect, a birthing system for augmenting expulsive uterine forces towards a cervical canal during delivery of a fetus from a uterus, includes a medical apparatus, a catheter, and a controller. The medical apparatus includes a balloon body configured to be placed in an intrauterine cavity at a location between an infant and uterine walls, and to be operated, e.g., expanded and contracted, there from. The balloon body is configured to transition between a compacted state and an expanded state. When in the expanded state the balloon body applies a force to a base of the fetus in a direction of the cervical canal. The catheter is configured to receive the medical apparatus, circumnavigate the fetus and one or more structures within the uterus to place the balloon body in the intrauterine cavity at the location between the infant and the uterine walls, and obtain electrical signals indicative of intrinsic uterine contractions. The controller is configured to monitor an intrinsic uterine contraction based on the electrical signals, and deliver or discharge agent to or from the balloon body to thereby mediate a force generated via the balloon body during the intrinsic uterine contraction.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Disclosed herein is a minimally invasive access catheter and method for gaining access to a proximal region of a uterus for the purposes of delivering, deploying and operating a peripheral intrauterine medical apparatus to assist infant descent during natural child birth. The catheter contains an internal lumen for supporting the medical apparatus during deployment.

The catheter is configured to circumnavigate an infant, umbilical cord, and uterine structures and to thereby allow for non-surgical access to the uterus in order to place the medical apparatus in line with the infant and birth canal during parturition. The catheter may also facilitate operation of the medical apparatus by providing physical support for a conduit body of the medical apparatus that delivers a pressurized gas or fluid agent to an expandable member of the medical apparatus. The catheter may also provide a biofeedback platform during the natural labor process. For example, the catheter may provide for the sensing of intrinsic uterine contractions through electrical sensors or mechanical sensors, e.g., pressure sensors, integrated with the catheter. The catheter can be used to place and operate the medical apparatus for prophylactic use and labor relief during early stage I labor, or upon diagnosis of abnormal labor or insufficient infant descent (dystocia, or the "failure to descend") due to insufficient uterine contractility during stage II labor.

In use, the catheter is inserted and advanced through the vaginal and cervical canal. The catheter contains a user operated steering mechanism to direct the distal tip of the catheter around intrauterine structures including the fetus, placenta, umbilical cord, to safely advance the catheter tip to a position near the fundus between the infant and endometrial lining near the proximal end of the uterine cavity. Upon accessing the target location, the medical apparatus configured to assist infant descent is deployed from the distal tip of the catheter. The catheter may be left in position throughout the duration of labor to provide physical support for the peripheral medical apparatus, and as a sensor platform for monitoring labor progress, maternal and fetal bio parameters. For example, the catheter may include electrodes that sense and conduct signals corresponding to uterine contractions and physiologic effects. Following delivery of the infant, the catheter may be used as a support structure for withdrawing the medical apparatus from the intrauterine cavity through the birth canal.

The peripheral medical apparatus may be a balloon apparatus such as described in co-pending U.S. patent application Ser. No. 14/942,748, titled "Intrauterine Balloon Apparatus, System, and Method for Augmenting Uterine Birthing Forces During Parturition", the entire disclosure of which is herein incorporated by reference. The balloon apparatus is configured to be at least partially contained within a lumen of the catheter, and is designed to slide out of the catheter lumen and the distal tip of the catheter during deployment and expansion. The balloon apparatus may be packaged in a compacted manner to reduce displacement volume and circumferential diameter during the placement procedure, and deployed and expanded into the uterine cavity by introducing a pressurized agent through a lumen of the balloon body into the balloon body. The internal surface of the catheter lumen may have a high lubricity to facilitate this deployment action and reduce friction between the lumen and the exterior of the balloon apparatus.

The catheter may include one or more spaced apart markers for measuring the depth of insertion by visual inspection, and differing reflective material properties for visualizing the catheter position relative to internal anatomical structures with the use of external ultrasound imaging equipment. The catheter may be utilized in conjunction with one or more additional barriers for preventing the catheter from introducing contaminants in the birth canal into the uterine cavity or infant(s). A mechanical or chemical barrier, such as a sheath or fluid gel based substance, shields the distal end and catheter body as it passes through the vaginal and cervical canals thereby reducing the likelihood of direct contact between the catheter and the walls of the birth canal as it reaches the uterine cavity.

Figure 1:
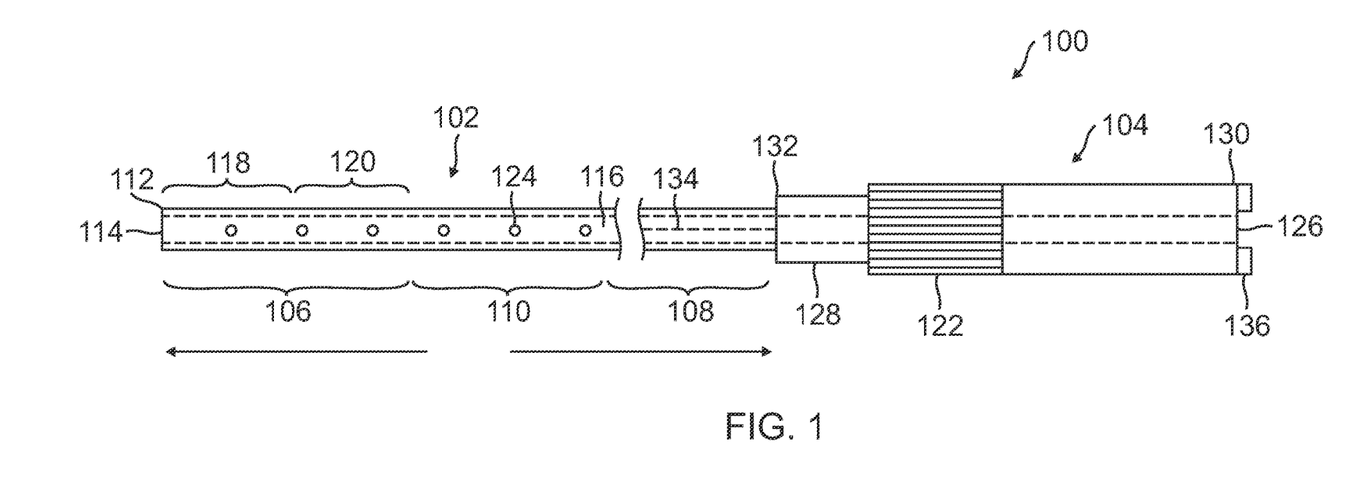
FIG. 1 is an illustration of an access catheter including an elongated body and a handle.

FIG. 1 is an illustration of an access catheter 100 including an elongated body 102 and a handle 104. The elongated body 102 includes a distal section 106 and a proximal section 108. The distal section 106 may have a length of about 2 centimeters (cm) to about 13 cm, and may include a distal portion 118 and a proximal portion 120. At least one of the distal portion 118 and proximal portion 120 may be formed with a curve (not shown) or configured to bend to facilitate entry within the patient's cervix.

The elongated 102 is configured so that the distal portion 118 is more flexible than the proximal portion 120, and the proximal portion is more flexible than the proximal section 108 of the elongated body. To this end, the distal portion 118 may be formed of a polymer material having a hardness of about 10 D to about 60 D (Shore); the proximal portion 120 may be formed of a polymer material having a hardness of about 30 D to about 80 D (Shore); and the proximal section 108 of the elongated body may be formed of a polymer material having a hardness of about 60 D to about 85 D (Shore).

The elongated body 102 may also include an intermediate section 110 between the distal section 106 and the proximal section 108. The intermediate section 110 may have a flexibility that is greater than the proximal section 108 and less than the distal section 106. The intermediate section 110 may have a hardness of about 30 D to about 60 D (Shore), and a length of about 1 centimeter to about 8 cm.

The handle 104 includes a proximal end 130, a distal end 132, and a proximal port 126 at the proximal end. A central lumen 116 extends from a port 114 at the distal tip 112 of the elongated body 102, through the entirety of the elongated body and the handle 104, to the proximal port 126 at the proximal end 130 of the handle 104. The central lumen 116 is configured to slidably receive a medical apparatus through the proximal port 126 at the proximal end 130 of the handle 104. In a configuration where the distal section 106 is curved, the distal port 114 in the distal tip 112 is directed away from a longitudinal axis 134 of the proximal section 108. The distal port 114 at the distal tip 112, and the proximal port 126 at the proximal end 130 of the handle 104 have a diameter equal to the diameter of the central lumen 116.

In some configurations, as described below with reference to FIG. 3, the catheter 100 may include sensors for providing signals corresponding to biological or physiologic activity. In such configurations, the handle 104 of the catheter 100 may include a connector 136 that provides for electrical connection between the sensors and a controller configured to process the signals.

Figure 2:
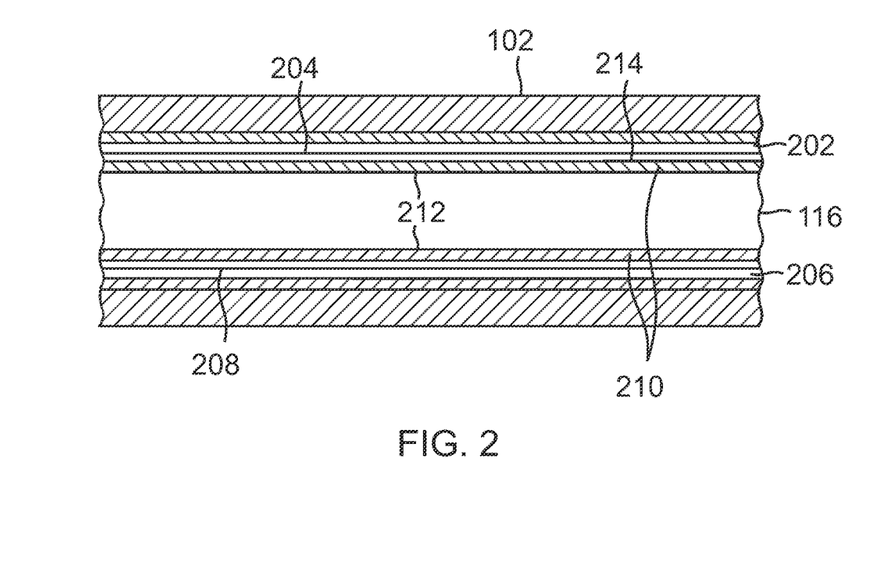
FIG. 2 is cross section illustration of the elongated body of the access catheter of FIG. 1.

FIG. 2 is cross section illustration of the elongated body 102 of the access catheter 100 of FIG. 1. The elongated body 102 includes a first or central lumen 116 traversing the entire length of the body. As described above with reference to FIG. 1, the central lumen 116 is configured to receive and contain a peripheral medical apparatus. The elongated body 102 also includes a second lumen 202 that contains a tension wire 204. As described further below, the tension wire 204 may be used to deflect the distal section 106 of the catheter. The elongated body 102 may also include a third lumen 206 that contains one or more insulated electrical wires 208. As described further below, the electrical wires 208 may electrically couple electrodes at the distal section 106 with a connector at the proximal end 130 of the elongated body. The size of each lumen 202, 206 is sufficient for its intended purpose.

The elongated body 102 is made of a flexible and resilient biocompatible material, such as a medical grade silicone elastomer, and includes a longitudinally extending tubular wall 210. The tubular wall 210 includes a radially inner surface 212 and a radially outer surface 214, both which extend the entire length of the elongated body 102. The inner surface 212 of the central lumen 116 has a low coefficient of friction to allow for ease in movement there through of a medical apparatus. With reference to FIG. 1, the central lumen 116 is open at the distal end of the central lumen and thereby defines the distal port 114 of the elongated body 102. The central lumen 116 is also open at the proximal end 130 of the handle and thereby defines the proximal port 126.

Figure 3:
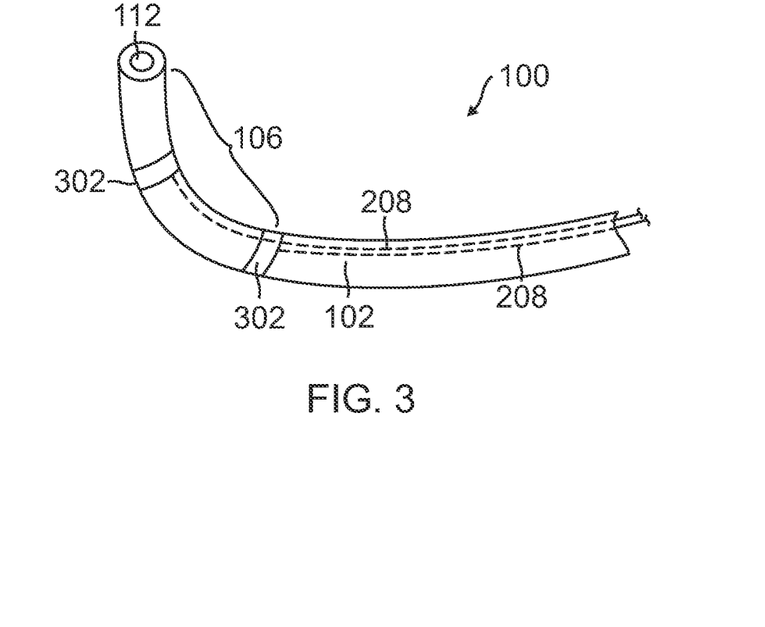
FIG. 3 is an illustration of a configuration of the access catheter of FIG. 1 including electrode sensors.

FIG. 3 is an illustration of a configuration of an access catheter 100 including electrical activity sensors. The electrical activity sensors may be a series of ring electrodes 302 mounted on the non-conductive surface of the elongated body 102 on or near the distal section 106. The ring electrodes 302 may be made of any suitable solid conductive material, such as platinum or gold, preferably a combination of platinum and iridium, and may be mounted onto the elongated body 102 with glue or the like. Alternatively, the ring electrodes 302 can be formed by coating the non-conductive surface of the elongated body 102 with an electrically conducting material, such as platinum, gold and/or iridium. The coating can be applied using sputtering, ion beam deposition or an equivalent technique.

The ring electrodes 302 are attached to electrical wires 208 traversing the length of the elongated body 102 and are coupled to the connector 136 associated with the handle 104. The electrical wires 208 are coated with electrical insulation layer and conduct electric signals received from the ring electrodes 302 to the connector 136. Electric insulation layer may be a coating, a film, or a tube-like component and may be comprised of, for example, Parylene, silicon nitride, silicon oxide, or Teflon.

The ring electrodes 302 may be mounted by first forming a hole in the elongated body 102. An electrical wire 208 is fed through the hole, and the ring electrode 302 is welded in place over the wire and the elongated body 102. The electrical wires 208 extend through the wall of the elongated body 102 and into a lumen 206 of the elongated body, such as the third lumen 206 shown in FIG. 2. The proximal end of each electrical wire 208 is electrically connected to the connector 136, which in turn, is connected to an appropriate controller or other device for receiving signals from the electrode. The controller is configured to process the electrical activity signals and to extrapolate uterine contraction states for providing guidance on the timing of operation of the medical apparatus deployed by the catheter. The location and spacing of the ring electrodes 302 are sufficient to sense local and global uterine contractions. In one arrangement, at least one electrode 302 is placed near the distal tip 112 of the elongated body 102 and another electrode is placed a sufficient distance to allow for discrimination of signals from noise and for monitoring of electrical activity indicative of uterine contraction onset and propagation.

Figure 4:
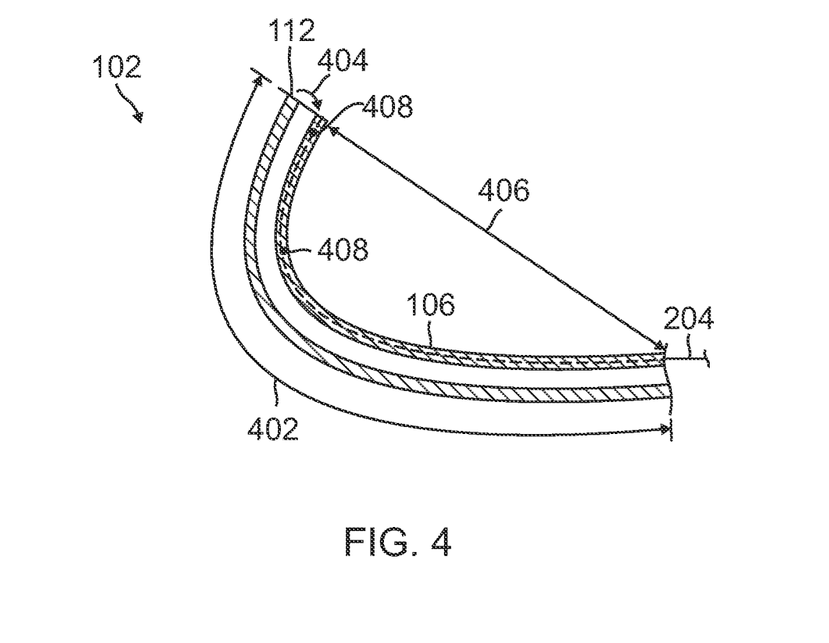
FIG. 4 is an illustration of a configuration of the access catheter of FIG. 1 including a deflectable distal section.

FIG. 4 is an illustration of a configuration of the access catheter 100 including a deflectable distal section 106. In this configuration, the distal section 106 is made of a suitable biomaterial of about 10 D to about 60 D (Shore) for softer deflectable capabilities and has a length 402 of about 5 cm to about 13 cm. Deflection 404 of the distal section 106 to a curvature 406 is accomplished by suitable tension from a tension wire 204 through movement of the manipulation mechanism 122 of the handle 104 resulting in longitudinal movement of the tension wire 204 relative to the elongated body 102. The distal section 106 may be fabricated of a flexible resilient material so that it tends to assume a particular shape when at rest.

The tension wire 204 is affixed at one or more attachment points 408 along the inner curvature of the distal section 106, resulting in an inward deflection of the distal tip 112 upon application of tension through the tension wire 204. Upon release of the tension from the tension wire 204, the distal section 106 assumes its original shape. The original shape by be straight or it may be curved. When a deflection force is imparted to the distal section 106 to achieve deflection 404, the inherent construction of the distal section exerts an opposing, or straightening restoring force, that tends to return the body member to its "at rest" shape. In the case of FIG. 1, the distal section 106 assumes a relatively straight shape when at rest. When enough tension is applied to the tension wire 204, deflection occurs but the body member applies an opposing straightening force. When all deflection forces have been removed from the distal section 106, this force created by the construction of the distal section returns the distal section to a straightened position.

As previously described, the tension wire 204 may be attached to the distal section 106 at one or more attachment points 408 along the length of the distal section. These attachment points 408 may be around the circumference of the distal section 106 to provide for a more uniform application of force across the catheter cross sectional area. Attachment points 408 located as such provide suitable strain relief and reduce the likelihood of damage to the elongated body 102 or lumens due to tension applied from the tension wire 204.

Figure 5:
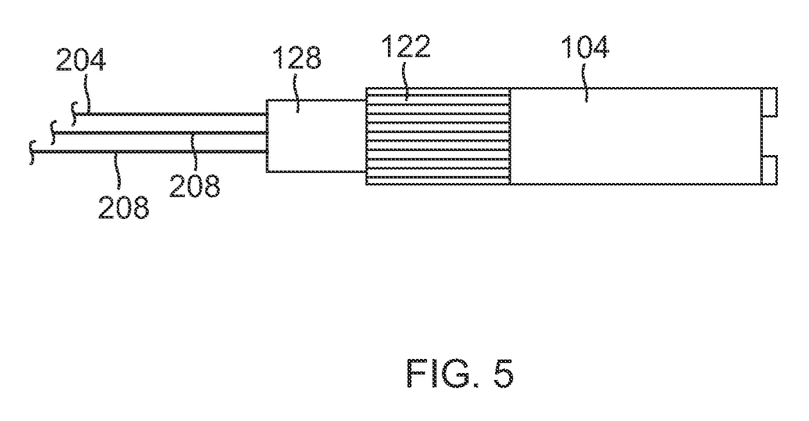
FIG. 5 is an illustration of a navigation controller for deflecting the distal section of FIG. 4.

FIG. 5 is an illustration of a navigation controller for deflecting the distal section of FIG. 4. The handle 104 includes a user controlled manipulation mechanism 122 attached to a tension wire 204. Operation of the manipulation mechanism 122 applies tension to the tension wire 204 for varying the deflection of the distal section. In one configuration, the manipulation mechanism 122 is a knob or circular control wheel on the handle 104, which enables the user to vary the amount of tension exerted on the tension wire 204 with the same hand used to hold the catheter without the need to reposition the hand. A locking mechanism 128 is provided in the handle for physically maintaining wire tension thereby fixing or "locking" the distal section in a deflection state.

Upon diagnosis of abnormal labor including slow infant descent due to insufficient uterine contractile forces, a birthing professional may decide that augmentation of intrinsic contraction forces may be beneficial. To this end the birthing professional may desire to employ a medical system configured for placement in the uterus for purposes of assisting infant descent during active labor of parturition. The medical system may include the catheter 100 described in FIGS. 1 through 5, and a medical apparatus. The medical apparatus may be as described in co-pending U.S. patent application Ser. No. 14/942,748, titled "Intrauterine Balloon Apparatus, System, and Method for Augmenting Uterine Birthing Forces During Parturition."

Figure 6:
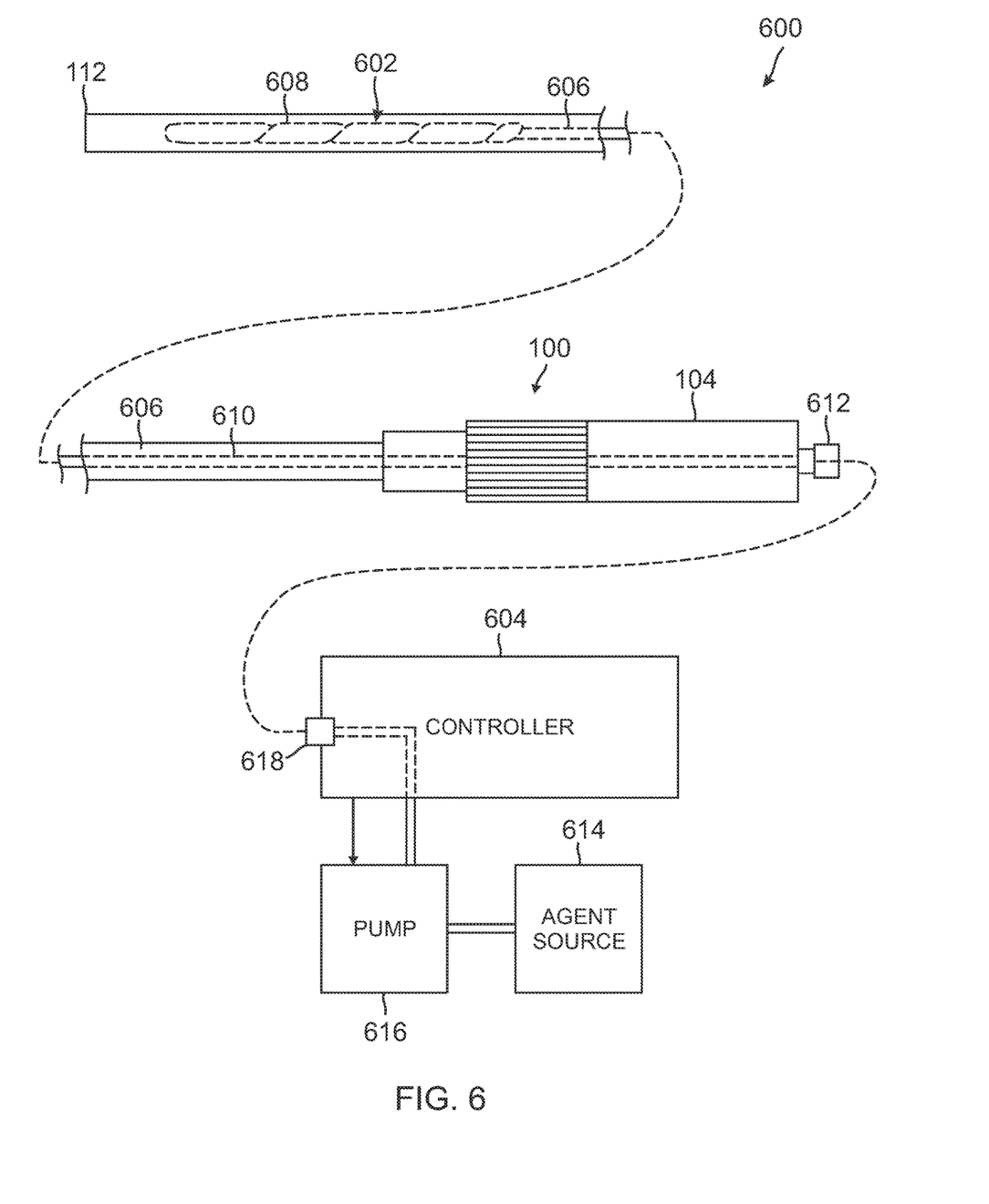
FIG. 6 is an illustration of a medical system including the access catheter of FIG. 1, a medical balloon apparatus placed within the catheter, and a controller.

FIG. 6 is an illustration of a medical system 600 including an access catheter 100, a medical balloon apparatus 602 placed within the catheter, and a controller 604. The medical balloon apparatus 602 include a conduit body 606 and a balloon body 608. The conduit body 606 includes a proximal region, a distal region, and an internal lumen 610. The balloon body 608 is coupled to the distal region of the conduit body 606 and has an internal chamber in fluid communication with the internal lumen of the conduit body. The balloon body 608 is configured to transition between a compacted state (shown in FIG. 6) and an expanded state (shown in FIG. 10).

The medical balloon apparatus 602 also includes a connector 612. The connector 612 is configured to connect the medical balloon apparatus 602 to the controller 604 and provide an interface between the internal lumen 610 of the conduit body 606 and an agent source, such as a fluid/gas source 614, associated with the controller. The fluid/gas source 614 may be associated with the controller 604 through a pump 616, which may operate under control of the controller 604. The conduit body 606 enables bidirectional agent conduction between the agent source 614 and balloon body 608 through the internal lumen 610.

The catheter 100 is used to place the medical balloon apparatus 602 in the intrauterine cavity. To this end, and with reference to FIGS. 1 and 6, the medical balloon apparatus 602 may be inserted into the central lumen 116 of the catheter 100 through the proximal port 126 of the catheter. The medical balloon apparatus 602 may be advanced through the central lumen 116 until the balloon body 608 is within either of the distal section 106 of the catheter or the intermediate section 110 of the catheter. Placement of the balloon body 608 in the distal section 106 may impede deflection of the distal section. Accordingly, it may be beneficial to place the balloon body 608 within the intermediate section 110. Once appropriately positioned within the catheter 100, the medical balloon apparatus 602 may be locked in place by the locking mechanism 128. The catheter 100 may then be used to place and deploy the medical balloon apparatus 602 in an intrauterine cavity.

Figure 7:
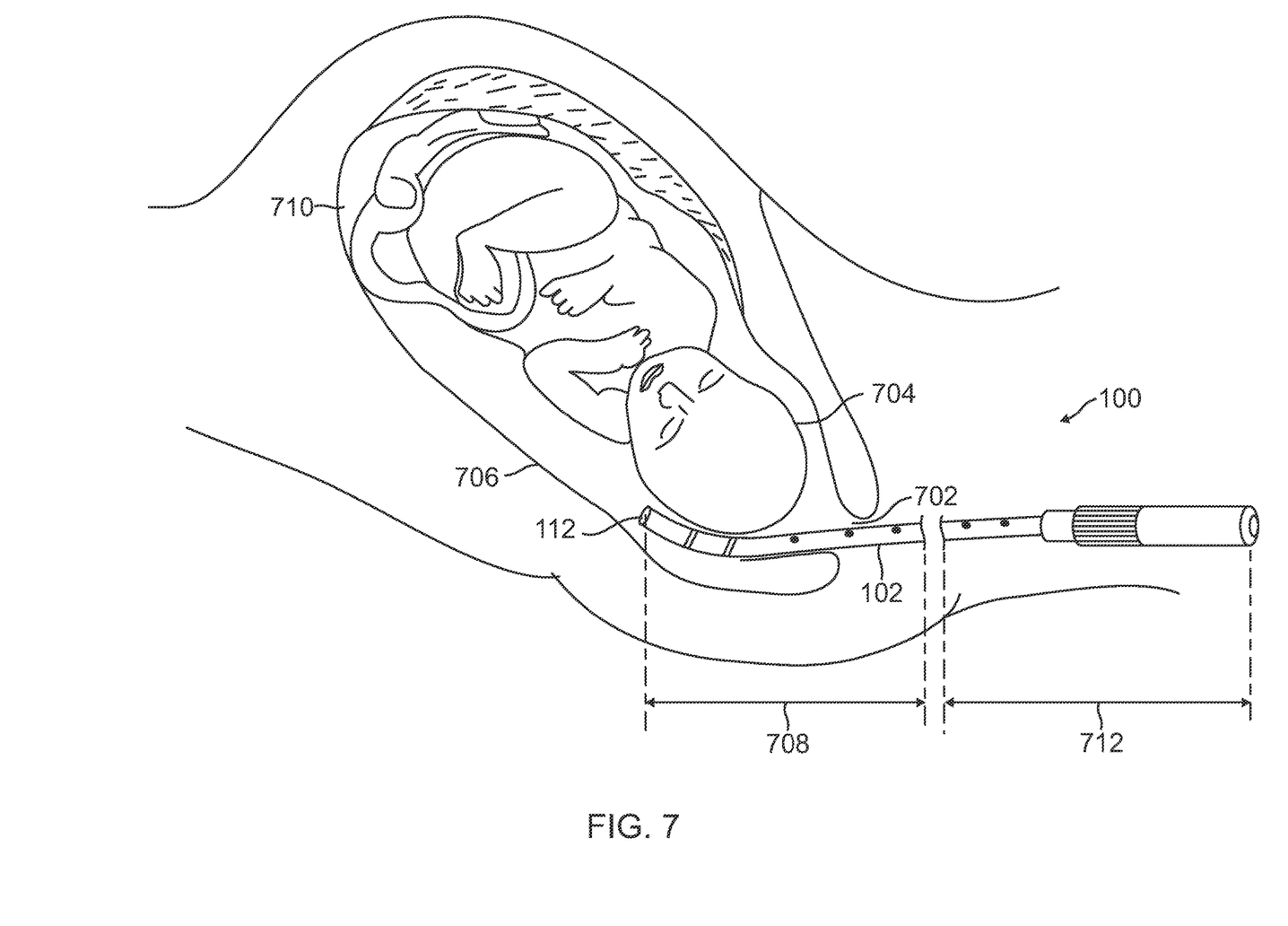
FIG. 7 is an illustration of an access catheter partially introduced in an intrauterine cavity.

FIG. 7 is an illustration of an access catheter 100 partially introduced in an intrauterine cavity. A user places the distal tip 112 of the elongated body 102 through the entrance of the birth canal cervical walls 702 of the patient and between the fetus 704 and the distal area of the uterine walls 706. The diameter of the elongated body 102 is sized for minimal displacement of internal uterine structures during the placement procedure and includes a sufficiently sized distal tip 112 for navigating a minimally intrusive pathway to the proximal area of the uterine cavity without the need to transect any internal membranes or organs. The length 708 of the elongated body 102 is sufficient to reach the proximal regions of the intrauterine cavity near the fundus 710 while providing sufficient externalized extracorporeal length 712 for manipulation and connection of the catheter by the user to a controller during the birthing procedure.

Figure 8:
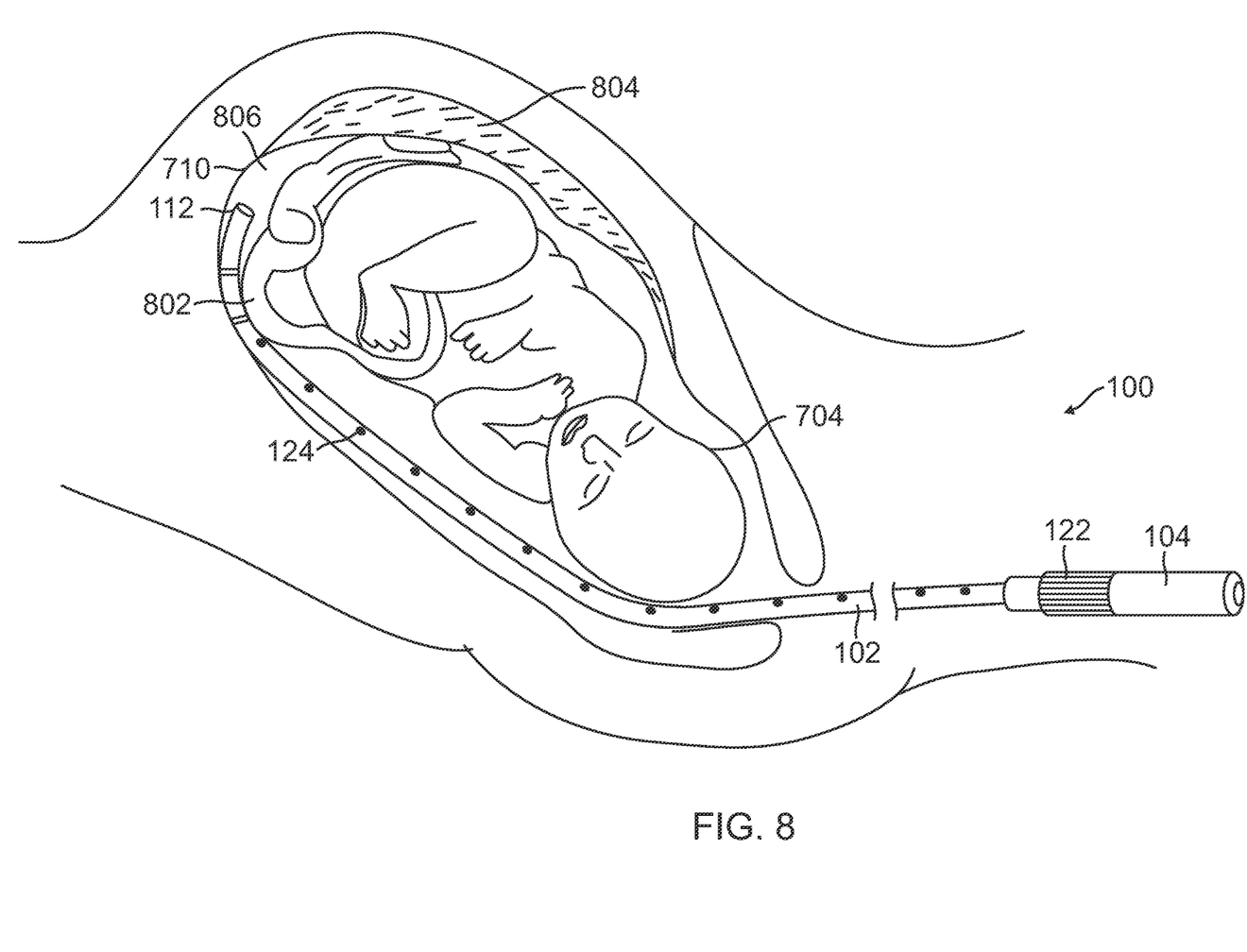
FIG. 8 is an illustration of an access catheter further introduced in an intrauterine cavity.

FIG. 8 is an illustration of illustration of an access catheter 100 further introduced in an intrauterine cavity. The user advances the catheter 100 along the uterine cavity walls to the target location near the fundus 710 of the uterus, safely circumnavigating structures within the uterine cavity including the fetus 704, umbilical cord 802, and placenta 804 to the proximal region 806 of the uterus. The user may navigate the catheter 100 using a combination of actions including rotating the handle 104 to rotate the entire catheter 100, manipulating the manipulation mechanism 122 to deflect the distal tip 112, and/or advancing and partially retracting the catheter 100 to direct the assembly towards the desired location. The user may be aided by visual and echogenic markers 124 located along the elongated body 102 for determining the inserted distance and the relative position of the distal tip 112. The elongated body 102 is sufficiently stiff to enable torque and reduce unwanted body flexion yet sufficiently pliable in order to conform without applying excessive focal contact pressures with internal organs, structures, or the infant during either access or navigation.

In one configuration, the distal tip 112 of the catheter 100 is made of a material with reduced hardness to reduce the likelihood of incurring damage to internal uterine structures, infant, or patient during delivery with a soft and rounded tip. As described with reference to FIG. 1, the elongated body may include different sections of different stiffness. An intermediate section 110 may have greater stiffness and less flexion properties than a distal section 106, and a proximal section 108 may have a greater stiffness than the intermediate section 110 for enabling efficient torque and advancement force transfer to the catheter body.

With reference to FIGS. 6 and 8, upon positioning of the distal tip 112 at the desired intrauterine location, the balloon body 608 may be advanced through the distal tip to allow for expansion of the balloon body. The balloon body 608 may be made to exit through the distal tip 112 by either pushing the conduit of the medical apparatus in a distal direction or by pulling the catheter 100 in a proximal direction or a combination of both. The balloon body 608 may also be made to exit through the distal tip 112 using pressurized agent. To this end, the connector 612 of the medical balloon apparatus 602 extending from the proximal port of the handle 104 may be connected with a coupler 618 of the controller 604 to create a hermetically sealed fluid communication path between the internal lumen 610 of the conduit body 606 and the controller for supplying pressurized agent from the agent source 614 to the balloon body 608 of the medical balloon apparatus 602. Once connected, agent may be delivered through the conduit body 606 to the balloon body 608. The pressure at the balloon body 608 imparts a force in the distal direction of the catheter 100 and causes the balloon body and conduit body 606 to slide in the distal direction. The force may be sufficient enough to cause the entire balloon body 608 to exit the distal tip 112 of the catheter 100.

Figure 9:
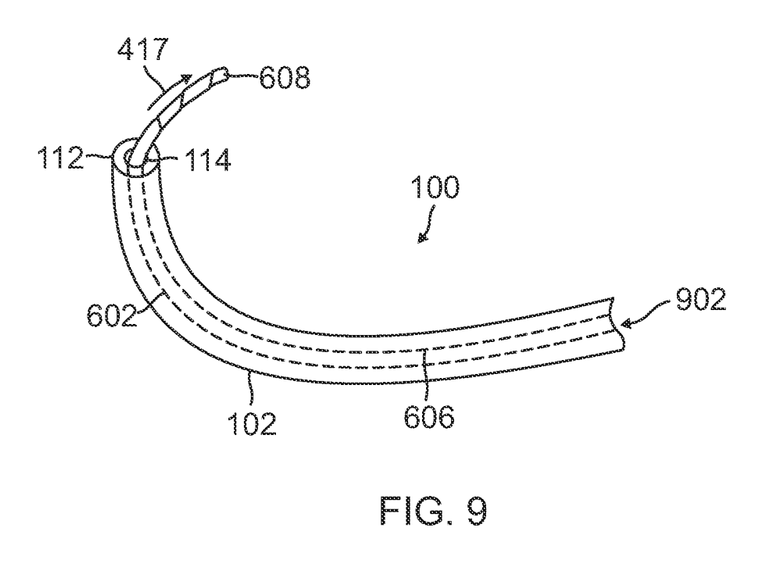
FIG. 9 is an illustration of a balloon body of a medical apparatus exiting an access catheter.

FIG. 9 is an illustration of a balloon body 608 of a medical apparatus exiting an access catheter 100 through the distal port 114 of the catheter. As just described, pressurized fluid air or gas injection 902 results in deployment of forces. Upon sufficient gas or fluid agent discharge, the medical balloon apparatus 602 may move relative to the elongated body 102 of the catheter 100 causing the medical balloon apparatus to displace towards the distal tip 112 of the catheter so that the compressed balloon body 608 may extend beyond the distal tip. Once the balloon body 608 exits the catheter 100, the rate of delivery of agent may be increased to thereby expand the balloon body to impart forces.

Figure 10:
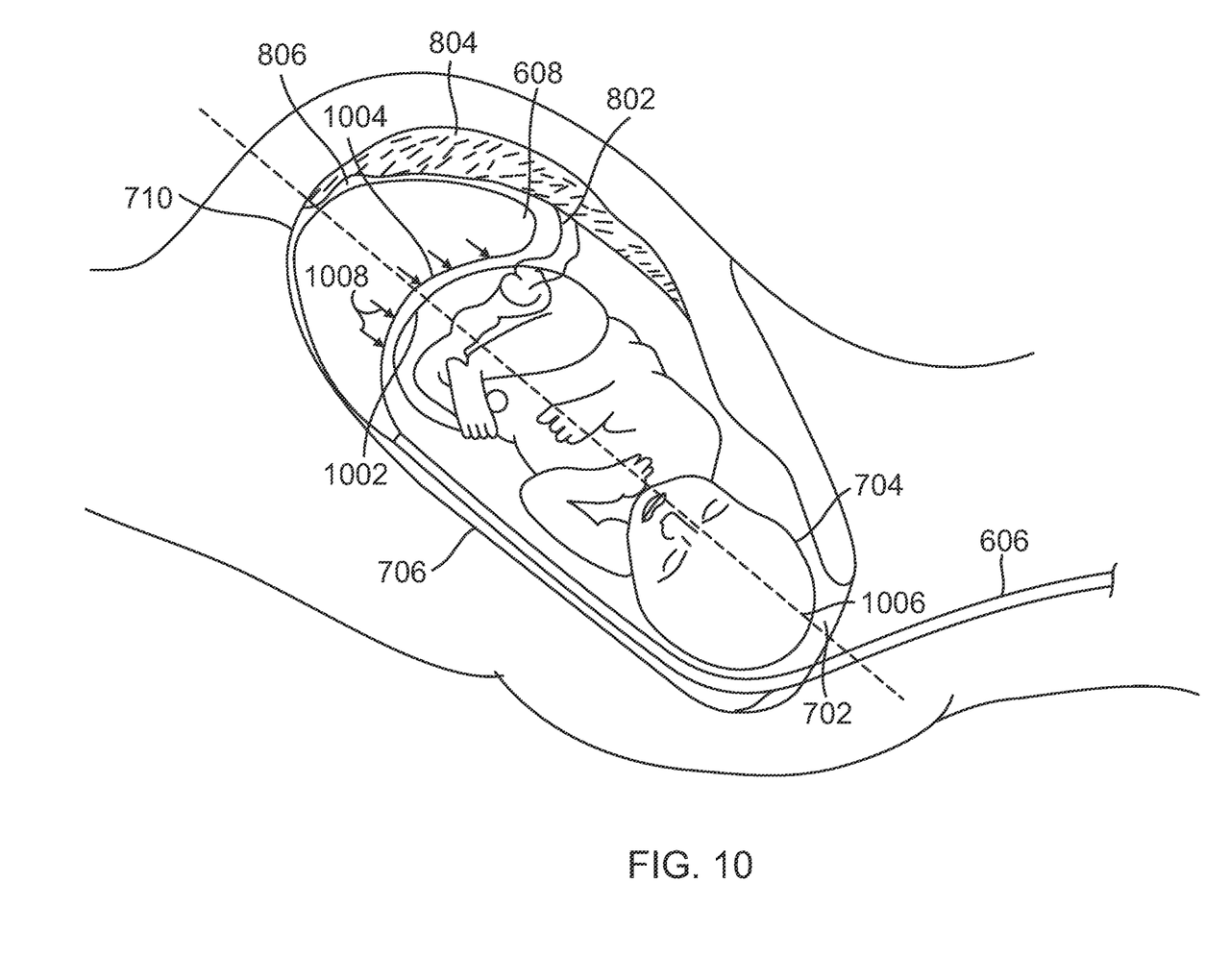
FIG. 10 is an illustration of the medical balloon apparatus of FIG. 9 positioned in an intrauterine cavity, in an expanded, deployed state.

FIG. 10 is an illustration of the medical balloon apparatus 602 positioned in an intrauterine cavity, while in an expanded, deployed state. FIG. 10 shows the balloon body 608 during expansion relative to the fetus 704, umbilical cord 802, placenta 804, uterine walls 706, and cervical canal 702. For clarity of illustration, the catheter 100 (shown in FIG. 8) used to place the medical balloon apparatus is not shown in FIG. 10.

Throughout inflation of the balloon body 608, a proximal wall 1004 of the balloon body faces the fetus 704 and cervical canal 702. Due to the designs of the balloon body 608, the balloon body predominantly expands in the direction generally along an axis 1006 passing through the uterus and the cervical canal 702. Accordingly, directional forces 1008 resulting from expansion of the balloon body 608 are applied to the base 1002 of the fetus. As the fetus 704 descends, the balloon body 608 is further expanded in order to maintain the application of the directional forces 1008. As such, directional forces 1008 are applied throughout infant descent through the cervical canal 702. Predominant expansion of the balloon body 608 in the direction along the axis 1006 in the direction of the cervical canal 702 reduces expansion of the balloon body in other directions. This is beneficial in that it reduces the amount of forces applied to other intrauterine structures, e.g., the uterine walls 706, and parts of the fetus 704 other than the base 1002.

Figure 11:
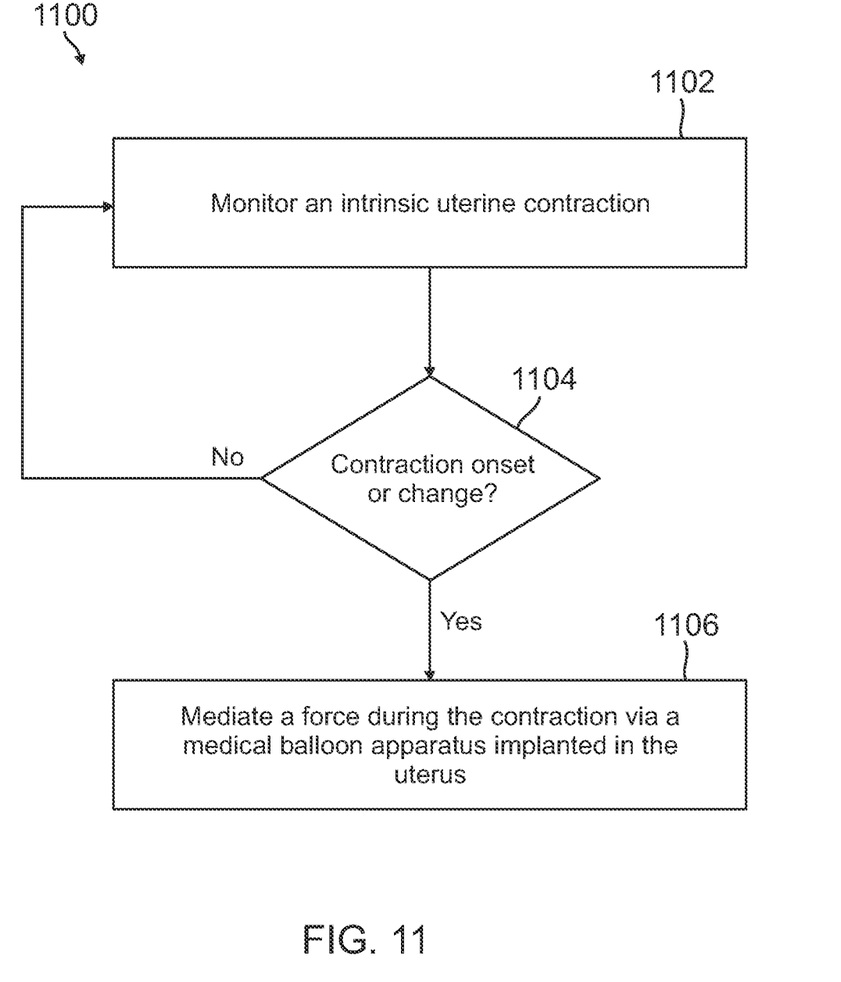
FIG. 11 is a flow chart of a method of augmenting expulsive uterine forces towards a cervical canal during delivery of a fetus from a uterus.

FIG. 11 is a flow chart of a method of augmenting expulsive intrinsic uterine forces towards a cervical canal during delivery of a fetus from a uterus. The method may be performed by the medical system 600 of FIG. 6.

At step 1102, the system 600 monitors an intrinsic uterine contraction. The intrinsic uterine contraction may be an onset of a contraction or it may be a change in state of an occurring contraction that results in either an increase in intrinsic intrauterine pressure or forces or a decrease in intrinsic intrauterine pressure or forces. The onset and pressure state of a uterine contraction may be monitored for by the controller 604 based on electrical activity sensed from the uterus and the processing of the sensed electrical activity. For example, morphology analysis of the sensed electrical activity may detect an onset of a contraction and changes in the pressure state of the contraction. The onset and pressure state of a uterine contraction also may be monitored for by the controller 604 based on sensed pressures. In one configuration, pressures are sensed through the conduit body 606, wherein such pressures are indicative of pressure within the uterus. In another configuration, an intrauterine pressure measurement may be obtained from a pressure sensor associated with a medical balloon apparatus 602 that is delivered in the uterus.

At step 1104, if an onset of an intrinsic uterine contraction or a change in state of an ongoing contraction is not detected by the system 600, the process returns to step 1102. If onset of an intrinsic uterine contraction or a change in state of an ongoing contraction is detected, the process proceeds to step 1106, where the system 600 mediates a force generated via a medical balloon apparatus 602 located in the uterus. The force is directed toward the cervical canal and augments natural expulsive uterine forces. In one configuration, the medical balloon apparatus 602 includes a balloon body 608 positioned at a proximal uterine location adjacent the fetus. For example, as shown in FIG. 10, the balloon body 608 may be positioned between the base 1002 of the fetus 704 and the fundus 710. The force is generated by delivering an agent to the balloon body 608 to thereby expand the balloon body toward the cervical canal 702 and into contact with the base 1002 of the fetus 704.

Upon either a detection of an onset of an intrinsic uterine contraction, or an increase in uterine contraction forces, the system 600 may mediate the force by delivering an agent to the balloon body 608 to at least partially expand the balloon body toward the cervical canal 702 and into contact with the base 1002 of the fetus 704. Upon a detection of a decrease in uterine contraction forces, the system 600 may mediate the force by discharging an agent from the balloon body 608 to at least partially collapse the balloon body away from the fetus 704 and the cervical canal 702. As a safety measure, the system 600 may also mediate the force by discharging an agent from the balloon body 608 when a measured pressure associated with the medical balloon apparatus exceeds a threshold value, such as 200 mmHg.

The forces applied by the medical balloon apparatus 602 are mediated by increasing and decreasing the agent delivered through the conduit body for constructively augmenting uterine pressures generated by intrinsic contractions. A target pressure or pressure based objective is set within the controller 604 and used to define the target balloon pressure resulting from agent delivery. To this end, the controller 604 may include a memory for storing program code and a processor that operates in accordance with the code to implement the process of FIG. 11. Accordingly, the controller 604 may be considered a special purpose computer that is configured to—in conjunction with a medical balloon apparatus 602 having a balloon body 608 configured to be positioned in the uterus—monitor an intrinsic uterine contraction, and mediate a force generated via the balloon body during the intrinsic uterine contraction, wherein the force is directed toward the cervical canal and augments natural expulsive uterine forces.

The controller 604 is further configured to implement subprocesses associated with monitoring and mediating. For example, the controller 604 may be configured to monitor an intrinsic uterine contraction by obtaining one or more of pressure signals and electrical signals indicative of an intrinsic uterine contraction. As described above, these signals may be provided by sensors associated with the medical balloon apparatus. The controller 604 includes program code that allows the processor of the controller to detect at least one of an onset of an intrinsic uterine contraction, an increase in uterine contraction forces, and a decrease in uterine contraction forces based on the one or more of pressure signals and electrical signals. To this end, the controller may process the signals to obtain corresponding measurements and compare the measurements to threshold values stored in memory that represent a contraction onset, or a change (e.g., increase or decrease) in uterine contraction force that warrants mediation.

With respect to mediation, the controller 604 may be configured to deliver an agent to the balloon body 608 to at least partially expand the balloon body toward the cervical canal and into contact with the fetus upon either of a detection of an onset of an intrinsic uterine contraction, or an increase in uterine contraction forces. The controller 604 may be configured to discharge an agent from the balloon body 608 to at least partially collapse the balloon body away from the fetus and the cervical canal upon a detection of a decrease in uterine contraction forces. As describe previously, an increase or decrease in uterine contraction forces may be warranted when the controller 604 detects a corresponding increase or decrease in pressure due to intrinsic uterine activity that satisfies a threshold criterion. The controller 604 may also be configured to discharge an agent from the balloon body 608 when a measured pressure associated with the medical balloon apparatus exceeds a maximum allowed threshold value.

The previous description is provided to enable any person skilled in the art to practice the various aspects described herein. Various modifications to these aspects will be readily apparent to those skilled in the art, and the generic principles defined herein may be applied to other aspects. For instance the handle for catheter navigation may be of various form factors or operational orientation, the connector to an external controller may bifurcate separating mechanical from electrical conduits and connectors, the cross sectional locations, number and sizes of internal lumens may vary to perform the stated functions, and the catheter may be physically connected to part of the deployed peripheral medical apparatus. Furthermore, nearly an infinite number of variations of electrode size and lengths, and/or catheter lengths and diameters may be utilized. These and other modifications obvious to those skilled in the medical apparatus arts are intended to be within the scope.

Disclosed herein is a catheter 100 configured to be delivered through the cervical canal, accessing the uterine cavity between the infant and mother's endometrium lining, for purposes of assisting birthing. In another configuration, the catheter 100 may be configured to be delivered through the maternal abdomen, accessing the abdominal cavity near the perimetrium of the uterus, for purposes of assisting birthing. In either configuration, the catheter 100 may be used as a conduit and/or diffuser for forces or pressure including hydraulic pressure, fluids including air, saline, lubricants, antibiotics or other substances, placing a medical device to target locations near the uterine walls, or combinations thereof.

The catheter 100 may include a sheath, guidewire, flexible tubing or other guidance system to assist navigation through the cervical canal and reaching a targeted intrauterine location. The catheter 100 may include a physical covering, sheath, outer lumen, or other antibiotic agent, for passage through vaginal or abdominal cavities, to reduce exposure of the catheter body itself to areas with higher risk of potential pathogens. The catheter 100 may utilize an inflatable diaphragm at the distal end of the catheter. The catheter 100 may incorporate one or more lumens for conducting fluids and/or providing desired handling properties of the catheter. The catheter 100 may include one or more sensors for detecting and monitoring uterine contraction timing, forces and effects from the abdominal muscles, myometrial uterine muscles, or other applied forces during labor. The catheter 100 may include one or more sensors for detecting and monitoring applied forces and their direction including those exerted by one or more medical devices, e.g., a medical balloon apparatus.

The catheter 100 may be made from a flexible, pliable, biocompatible material including but not limited to silicone, polyurethane, polyvinyl chloride, polyethylene or polytetraflouroethylene (Teflon), and combinations or blends thereof. The catheter 100 may be attached at the proximal end to a reservoir, tubing, or relief valve for delivering fluids or conducting forces into the distal tip, at one or more points along the birth canal, or into a separate medical device. The fluids delivered include lubricants, antibiotics, air, synthetic hormones, biosimilars, or saline. The catheter 100 may be attached to an external medical device, e.g., a controller, utilizing the information measured from a sensor integrated into the catheter for detecting applied forces and their direction in the uterus, infant(s), or combination thereof. The catheter 100 may be configured to enable visualization within intrauterine cavity of physical relationships between the uterine wall, birth canal, one or more fetus(es), placenta, or umbilical cord(s), during delivery. The catheter 100 may be configured to conduct or transmit data from sensors to a controller having hardware designed to filter, process, analyze and display or incorporate into an algorithm. The catheter 100 may be attached to an inflatable balloon or other plessary device at the proximal end of the catheter for the purpose of cervical ripening. The catheter 100 may be used during the prepartum or intrapartum stage of the birthing process.

Thus, the claims are not intended to be limited to the aspects shown herein, but is to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

What is claimed is:

1. A system for augmenting expulsive uterine forces towards a cervical canal during delivery of a fetus from a uterine cavity, the system comprising:
   a balloon body configured to be placed in the uterine cavity;
   a sensor configured to obtain electrical signals indicative of intrinsic uterine contractions; and
   a controller configured to:
      detect one of an onset of an intrinsic uterine contraction, an increase in uterine contraction forces, and a decrease in uterine contraction forces based on the electrical signals,
      responsive to either of a detection of an onset of an intrinsic uterine contraction or an increase in uterine contraction forces, at least partially expand the balloon body, and
      responsive to a detection of a decrease in uterine contraction forces, at least partially collapse the balloon body.

2. The system of claim 1, further comprising an agent source coupled to the controller and in fluid communication with the balloon body, wherein the agent source holds an agent and the controller is configured to at least partially expand the balloon body by causing agent to be delivered from the agent source to the balloon body.

3. The system of claim 2, wherein the controller is configured to at least partially collapse the balloon body by causing agent to be discharged from the balloon body.

4. The system of claim 3, wherein the agent is discharged into the agent source.

5. The system of claim 1, wherein the balloon body is configured to be placed in a region of a fundus near a proximal end of the uterine cavity between the fetus and endometrium lining.

6. The system of claim 1, further comprising a catheter configured to be placed in the uterine cavity, wherein the sensor is associated with the catheter.

7. The system of claim 1, wherein the controller is further configured to:
   obtain an intrauterine pressure measurement;
   compare the intrauterine pressure measurement to a threshold; and
   responsive to the intrauterine pressure measurement exceeding the threshold, cause agent to discharge from the balloon body.

* * * * *